United States Patent [19]
Cox

[11] Patent Number: 5,433,697
[45] Date of Patent: Jul. 18, 1995

[54] CONFORMABLE BACK BRACE WITH ABDOMINAL SUPPORT

[76] Inventor: Michael F. Cox, 10138 Lexington Estates Blvd., Boca Raton, Fla. 33428

[21] Appl. No.: 170,500

[22] Filed: Dec. 20, 1993

[51] Int. Cl.6 ............................................. A61F 5/00
[52] U.S. Cl. ................................. 602/19; 128/96.1; 128/115.1
[58] Field of Search .................... 602/5, 6–8, 602/19; 128/96.1, 112.1, 115.1; 2/44, 45, 92

[56] References Cited

U.S. PATENT DOCUMENTS

| | | | |
|---|---|---|---|
| 2,181,689 | 11/1939 | Bell | 602/19 |
| 2,813,526 | 11/1957 | Beebe | 602/19 |
| 2,828,737 | 4/1958 | Hale | 602/19 |
| 3,871,367 | 3/1975 | Miller . | |
| 4,173,973 | 11/1979 | Hendricks . | |
| 4,508,110 | 4/1985 | Modglin . | |
| 4,541,419 | 9/1985 | Osawa . | |
| 4,572,167 | 2/1986 | Brunswick . | |
| 5,074,292 | 12/1991 | Cox . | |
| 5,232,424 | 8/1993 | Pearson et al. | 602/19 X |
| 5,259,831 | 11/1993 | LeBron | 602/19 X |
| 5,295,947 | 3/1994 | Muncy | 602/19 X |

FOREIGN PATENT DOCUMENTS

| | | | |
|---|---|---|---|
| 1037220 | 9/1953 | France | 602/19 |
| 21866 | 11/1993 | WIPO | 602/19 |

OTHER PUBLICATIONS

DuPont Company, Fabricated Products Department, Lucite Acrylic Sheet.
E&T Plastics of Florida performance sheet and ad for Wrist Shots.
P.R. flyer, manufactured & distributed by CMO, Inc.
Simonds, Weith, and Bigelow, "Handbook of Plastics," 2nd Ed.
Alimed Mold-In-Place Back Support Sales Brochure.

Primary Examiner—Linda C. M. Dvorak
Attorney, Agent, or Firm—Malin, Haley, DiMaggio & Crosby

[57] ABSTRACT

A brace of supporting both the abdomen and lower back of the user. The brace includes a preformed abdominal support member and a preformed lumbar support member having an ideal lumbar shape with a dome, the support members each joined by two belts. The belts are positioned though slots on each member and are used to select the biasing force need for each user. The device further includes rounded corners with indented edges and surface vents on each support member for the user's comfort during sporting events or strenuous activity.

4 Claims, 5 Drawing Sheets

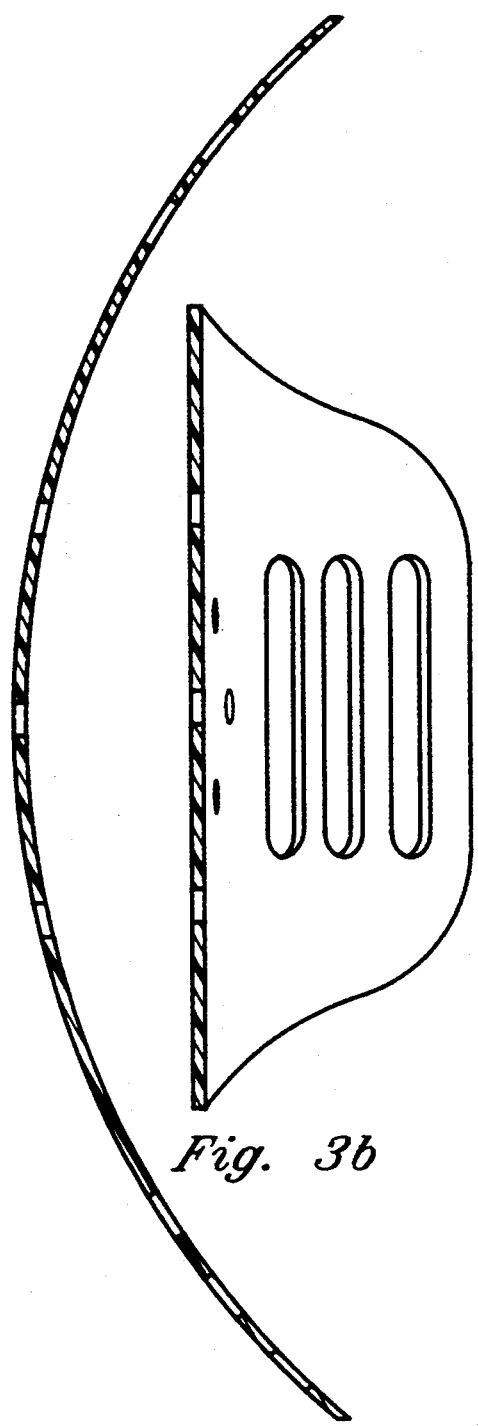
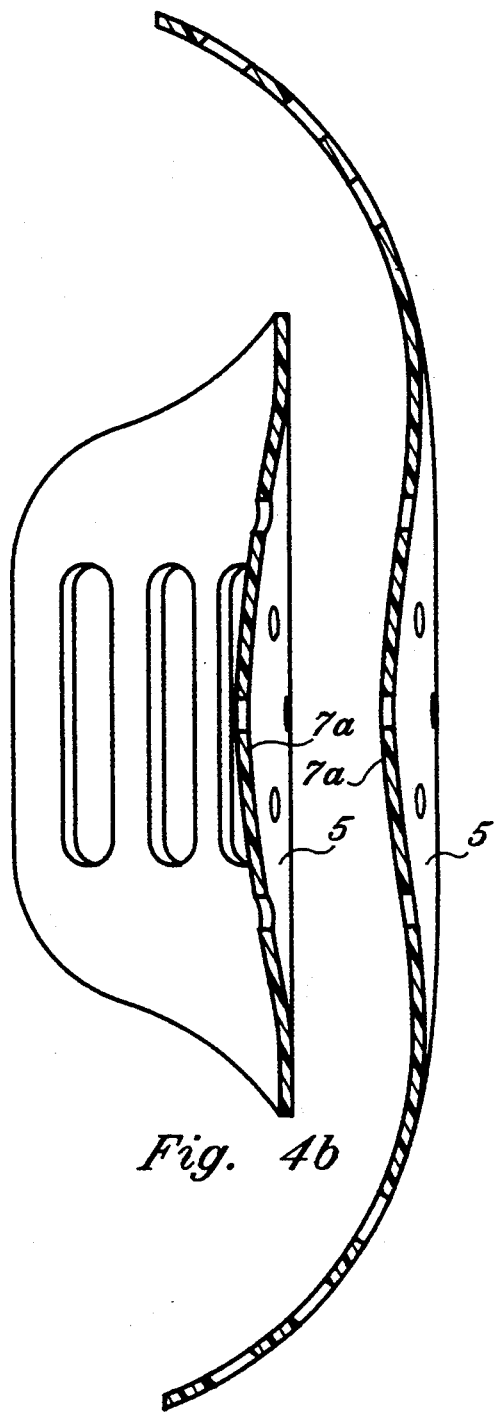
Fig. 3b    Fig. 4b
Fig. 3a    Fig. 4a

CONFORMABLE BACK BRACE WITH ABDOMINAL SUPPORT

BACKGROUND OF THE INVENTION

1. Field of the Invention

The present invention relates to a two component brace primarily intended for providing immobilization of the human back and more particularly to a brace for providing an ideal back profile and simultaneous abdominal and lumbar support to the user to realign and tone muscles around the back and stomach.

2. Description of the Prior Art

Spinal and lower back muscular pain is a common problem in many individuals. This type of pain, particularly among older or overweight individuals, can easily be aggravated during any type of body trauma such as heavy lifting or strenuous physical activity.

Prescription drugs must often be used to alleviate lower back pain which may not always be effective. Day to day activity requires movement of the back which can lead to further muscular aggravation, only to reach the point where all but the most potent pain relief medication is needed to have any effect.

In order to help alleviate lower back pain, prevent injury or aid in recovery, it is necessary to utilize a device which can provide support to the lower back to prevent muscular strain. In the past, many types of apparatus have been provided which help with this problem. These devices range from wrap-type supports to individual solid support fixtures placed longitudinally along the back to restrain movement. Many of these devices are either very heavy, too hot to wear, burdensome by unduly restricting movement or do not provide the proper support and alignment to be useful.

Recent research has determined that the most effective lumbar support occurs when the abdominal area of the user is supported as well. U.S. Pat. Nos. 4,572,167 and 4,508,110 teach support devices which wrap around the user's body but do not provide adequate abdominal and lumbar support due to the flexibility of the material used in construction and the methods of attachment. U.S. Pat. Nos. 4,173,973, 4,541,419 and 3,871,367 teach devices which are awkward to wear and are incapable of simultaneous abdominal and lumbar support. Applicant's prior U.S. Pat. No. 5,074,292 issued December, 1991 shows a back brace that can be form fitted to the individual. Although the device worked well, the present invention is an improvement that substantially uses an ideal lumbar configuration for improved muscle support.

Thus, it is apparent from these types of prior art devices that it was necessary to provide a device which would provide simultaneous lumbar and abdominal support and alignment which is light, comfortable, and easily adjustable. The device should also lend itself to be worn not only while sedentary but during strenuous physical activity such as golf, tennis or other sports, or in the work place while one sits for long periods or any physical work is required.

SUMMARY OF THE INVENTION

In accordance with the present invention, there is provided a two component brace which includes both an abdominal support and a lumbar support member. Each member is manufactured of a preformed plastic that is shaped as an ideal body contour for the respective body location. The lumbar support member includes a strategically shaped center dome located in the lower lumbar region for ideal back curvature and alignment of muscles and spine. In view of the substantially thin size of the brace, the brace can easily be worn within or outside a user's clothing.

Each support member includes rounded edges which are tapered for a comfortable fit along with a plurality of torso-encompassing belt adjustment slots positioned at each end of each member. These slots are used to engage separate fastening belts on each end thereof. Each belt is made of a durable lightweight fabric having some elasticity with hook and loop fastener materials secured thereto. Each end of each belt is then positioned through a selected one of the plurality of adjustment slots on each member where each belt, engages with itself, to form small loops at each respective end. This enables both the abdominal and lumbar support members to be engaged separately to hold and shape both of the members firmly against the user. Additionally, in order to allow body heat to escape from under the support members, a plurality of holes are placed about each support surface to allow body heat to escape.

The lumbar support device has a mid portion that is fairly flat or just slightly curved, with a central dome area that has a hemispherical shape or dome shape raised to face convexly when pressed against the lower lumbar region of the user. The dome is sized approximately $\frac{1}{4}''$ above the planar portion of the surface and approximately $3\frac{1}{2}''$ in diameter and is centrally located in the support member. The ends of the lumbar support member are curved as they would reach around the body of the user and include tapered end portions for comfort when the device may be pulled tight around the user for its curved edges and tapered end portions. With the dome convex protrusion, the overall shape of the lumbar support member is based on an ideal back configuration so that the muscles are aligned in the user and the spinal shape of the user is based on an ideal standard. This will allow the user's muscles to achieve close to an ideal conditioning and toning through continued use of the device.

The front abdominal support member basically is curved much as the front of the body is curved to provide a flush support area and is quite large, extending at least 6'' in height and approximately 15'' in overall length to extend to the outer edges of the front of the body.

The two adjustment bands include elasticized portions for some give so that there is some elasticity in wearing the device fairly tight to give body movement to the wearer so that it is not totally confining. In fact, a wearer can participate in sports such as golf, where there is quite a bit of body movement during a shot, or other sports.

Adjustment for various sized individuals is also accomplished so that the device can be worn flush to get the proper body support and configuration, both in the lumbar region and in the front region by having fabric hook and loop fasteners that allow individual adjustment along the straps on each side and with the variable adjustment slots as provided. The overall fit can be somewhat universal with a 25'' waist to a 54'' waist with the radius of curvature of the support members being approximately $8\frac{1}{2}''$.

By using the preformed ideal lumbar support in which the convex area nestles in the lower lumbar area of the back in conjunction with the abdominal and front support, alignment and toning of the muscles is achieved for great comfort while wearing and muscle strain is alleviated while the abdominal area is provided with contractive muscular support that supports the abdominal region with the overall effect of greatly reducing strain on the lower back area.

In accordance with these and other objects which will become apparent hereinafter, the instant invention will now be described with particular reference to the accompanying drawings.

BRIEF DESCRIPTION OF THE DRAWINGS

FIGS. 3a and 3b illustrate cross-sectional views of the abdominal support member shown through lines IIIa—IIIa and IIIb—IIIb shown in FIG. 2, respectively.

FIGS. 4a and 4b illustrate cross-sectional views of the lumbar support member shown through lines IVa—IVa and IVb—IVb shown in FIG. 2.

DESCRIPTION OF THE PREFERRED EMBODIMENTS

Figure 1:
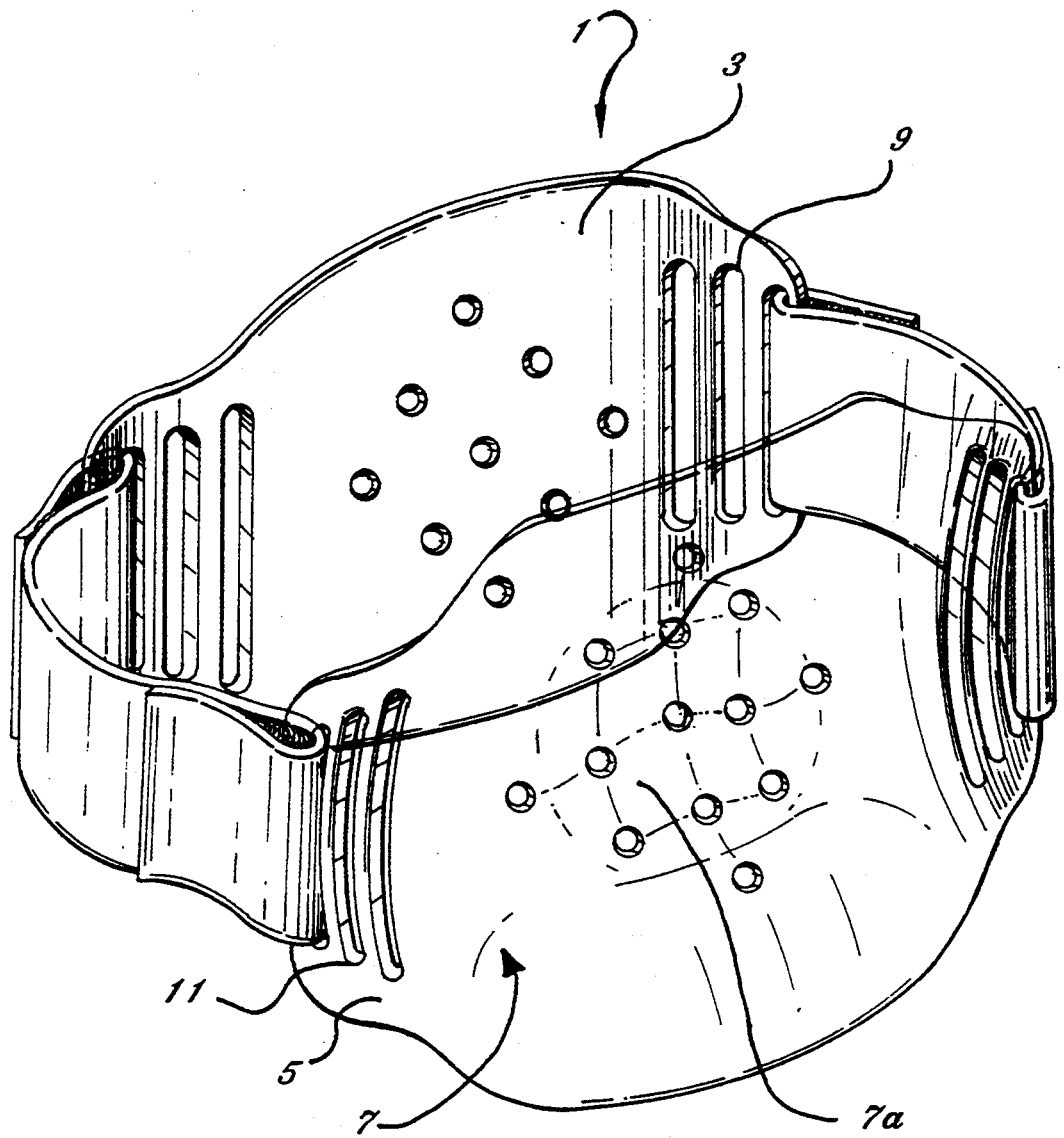
FIG. 1 illustrates a back perspective view of the invention, the support members being transparent plastic.

With reference to FIGS. 1-6, the two component back brace with abdominal and lumbar support members is generally shown at 1. The invention includes an abdominal support member 3 and a lumbar support member 5. FIGS. 3a and 3b show sectional views of the abdominal support member 3 while FIGS. 4a and 4b shows sectional views of the lumbar support member 5. Although both the abdominal support member 3 and lumbar support member 5 are generally convex in shape to conform to the peripheral torso shape of a human being in front and back body areas, the lumbar support member 5 includes a convex dome or hemisphere area 7 which is substantially at the center of the lumbar support member. The dome protrudes into the lower central lumbar back of the wearer to provide the ideal human back contour and extends longitudinally across the surface of the lower back. As best seen in FIGS. 4a and 4b, the lumbar support area 7a is that area of the lumbar support member 5 which extends inwardly, at the back's lower lumbar region.

This region of the lower back is often the most troublesome since it is difficult to support this area due to its shape. A major advantage to the instant invention is the type of material and the specific dome shape used to conform both the abdominal and lumbar support members 3,5 to all user's. First, in the preferred embodiment, both the abdominal support member 3 and lumbar support member 5 are manufactured of VIVAK ® Thermoplastic approximately 1/16 inch thick. Each lumbar support is pre-molded to the shape of a perfect back, in a small, medium and large size.

Both the abdominal support member 3 and lumbar support member 5 include at least three vertical slots, 9 and 11 respectively, which are positioned at each end of the members. Each slot is wide and high enough to accommodate fastening belts 13 and 15 to bias the support members snugly against the user. One slot at each end is selected to fit the support members properly around the torso. This allows the fastening belt to move within the slot to more easily adjust the belt when in use. Overall, the slots allow for a wide range of movement to accommodate various sizes of users.

Figure 2:
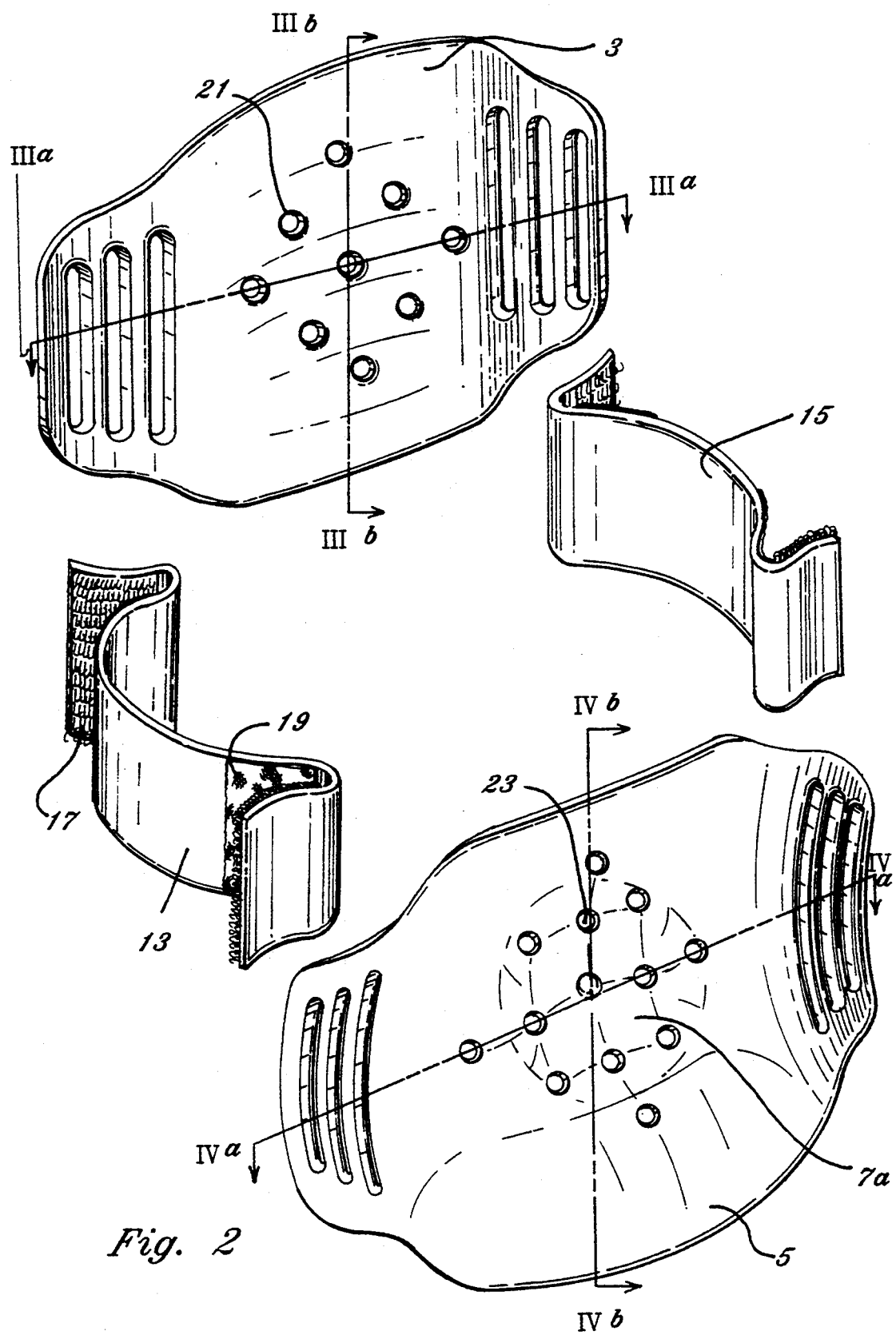
FIG. 2 illustrates a back exploded perspective view of that shown in FIG. 1.
Figure 5:
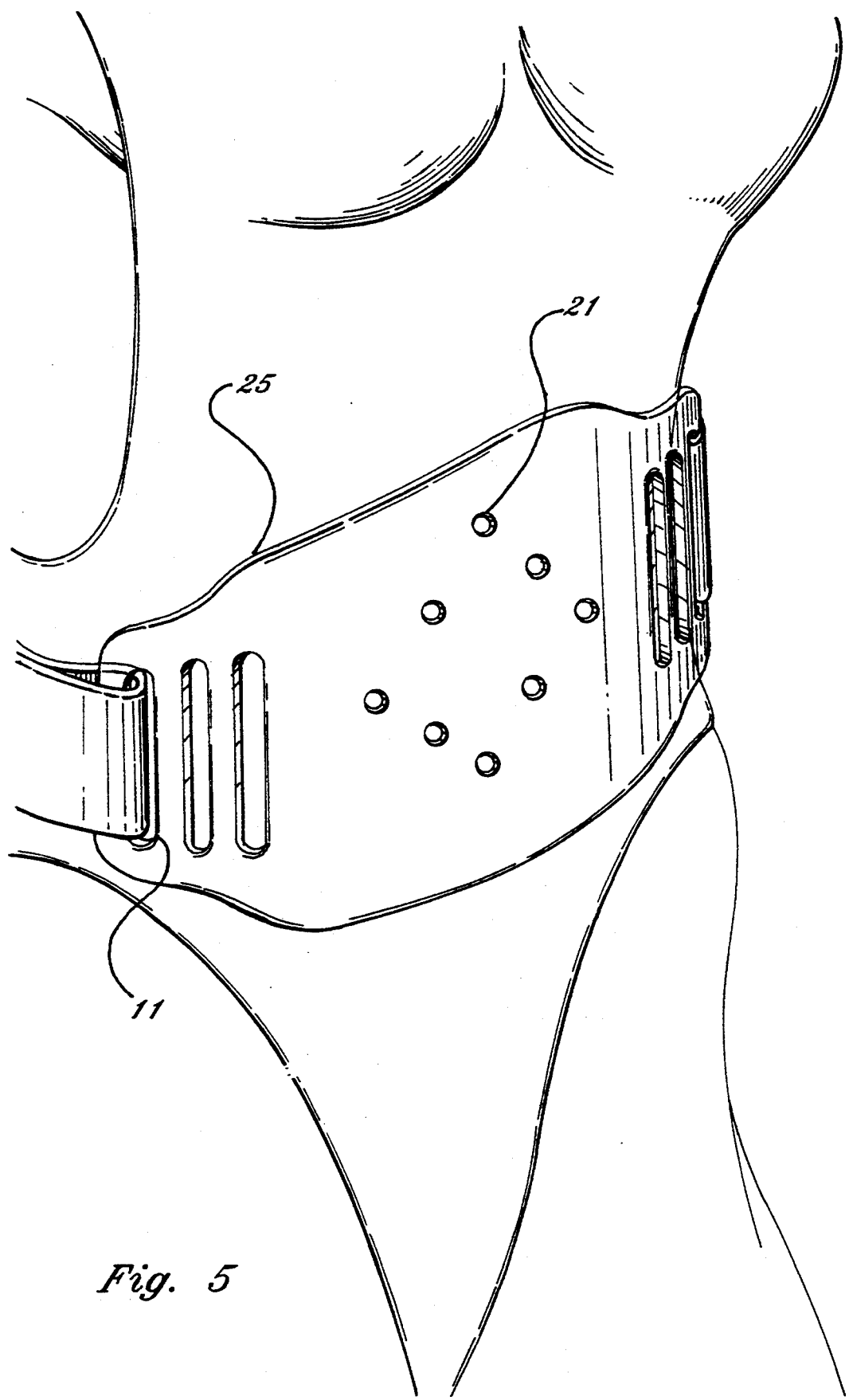
FIG. 5 illustrates a front perspective view of the abdominal support member as positioned on the abdomen of the user.
Figure 6:
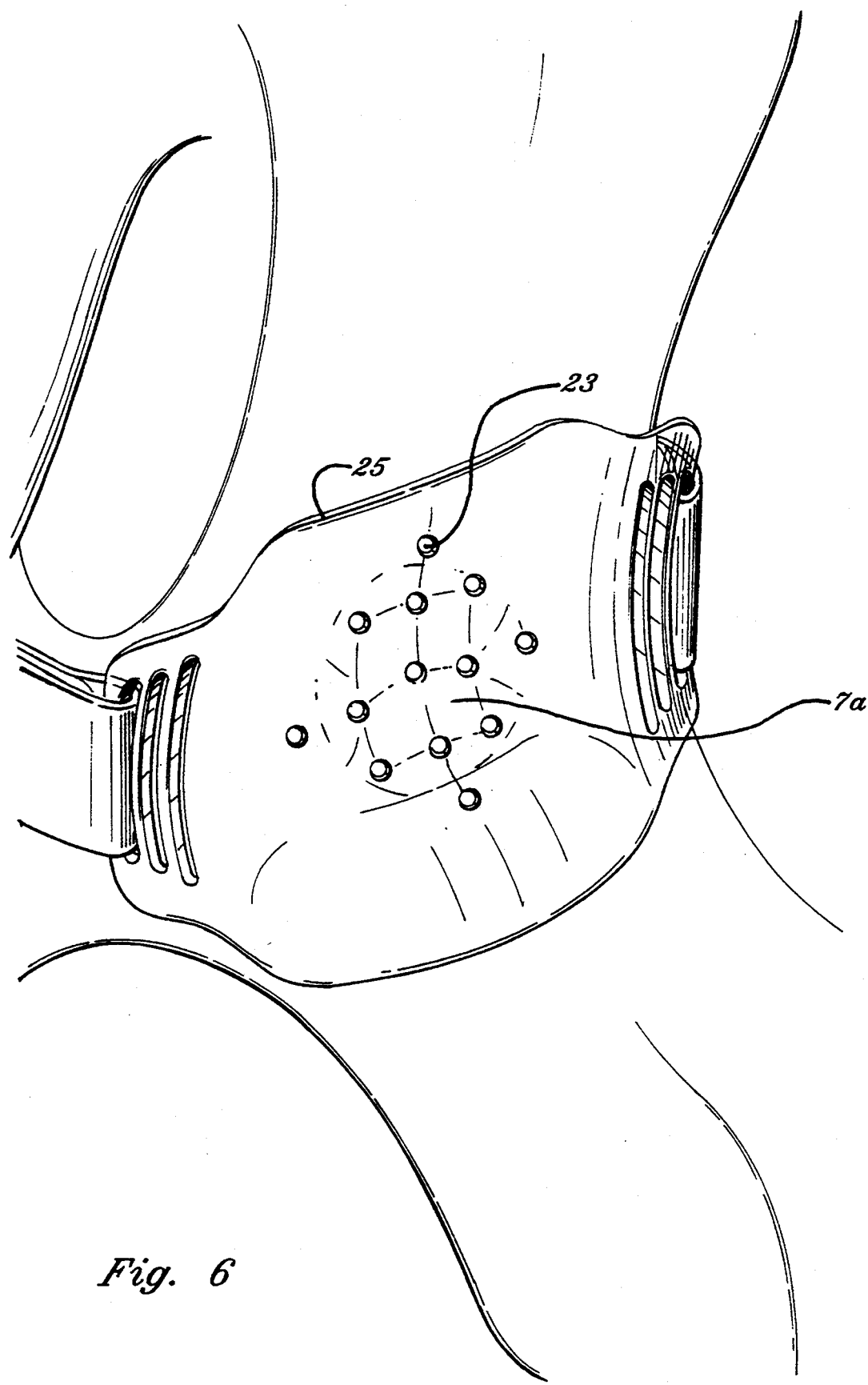
FIG. 6 illustrates a rear perspective view of the lumbar support member as positioned on the lower back of the user.

As seen in FIG. 2, the left fastening belt 13 and right fastening belt 15 are preferably made of a light weight, heavy duty nylon which aids in making the device lightweight and comfortable to wear. Each belt 13 and 15 includes hook fastening material 17 and loop fastening material 19 secured at each end to securely hold the belt, through one of the plurality of adjustment slots, upon itself. This is best seen in FIG. 1 where each end of each belt is folded back upon itself forming a small loop. Although hook and loop material is used in the preferred embodiment, it is easily recognized by those skilled in the art that any type of rigid fasteners, such as snaps or the like, could be used.

Additionally, both the abdominal support member 3 and lumbar support member 5 are substantially rectangle in shape and include rounded corners 25 which are tapered. This enables the user to securely fasten the brace around the torso, applying as much biasing force as needed using the left and/or right fastening belts 13,15, without unwanted forces pressing into the user's body. Without these tapered end corners 25, the brace would quickly become uncomfortable due to excessive force applied at these pressure points.

Finally, the abdominal support member 3 and the lumbar support member 5 include a plurality of vents. Both abdominal support vents 21 and lumbar support vents 23 prevent an excess buildup of body heat under each member and allows air to circulate under each respective member when it is needed most, viz. exercise or strenuous activity.

When looking at the lumbar support member in FIGS. 4a and 4b, the overall shape is somewhat circular resembling the overall shape of the body. However, the central portion 7a of the lumbar support area support member 5 includes a 3½ inch in diameter centrally positioned recessed or convex dome 7a that protrudes into the back lumbar area of the lower lumbar region of the user which is believed to be the ideal back position contour at the central portion of lumbar region for both the muscles positions in the back area and the spine position. By using an ideally preformed rigid support member the back muscles will seek the ideal configuration and conformance best suited for the human body to tone the muscles to alleviate muscle strain in the lower back area. Simultaneously, as shown in FIG. 3a the front member is somewhat circular having a radius of approximately 8½ inches to fit snugly around the stomach area to support the abdominal muscles in the abdominal area. Each of the braces are approximately 5 inches high and 9 inches in length and 1/16 inch thick made of thermal plastic that is basically rigid but does have a little bit of pliability for comfort and safety sake. The lumbar support member is in its central configuration somewhat flat with the exception of the dome protrusion but is curved near the end portions as it protrudes around the sides of the individual for comfort. There are several advantages presented by the present invention especially with respect to relieving muscle strain in the lower back area. By providing the ideal configuration for the human back as a support guide, muscles will be toned and the back lumbar region will be aligned in its proper location so that through the use of the device muscles will be trained and supported in the proper position. At the same time, the abdominal area is providing a contractive support that provides the proper front muscular support in the abdominal region with the overall result of greatly reducing strain on the lower back area and greatly enhancing muscle tone and realignment of various lumbar muscles. The device permits the stomach to be pulled in and the stomach to also achieve an appropriate configuration. The depth of the dome should be approximately ¼ inch so that it can nestle in the lower lumbar area of the back with a 3½ inch dome or hemisphere. The device can be made in what would be called small, medium and large because of the vast adjustability of the side belts and can generally fit human beings from a 25 inch waist to a 54 inch waist.

The belt straps 13 and 15 include some elastic portions 13a and 15a which are safety precaution to give some stretch in the belt for the benefit of the wearer. Using the present device with the tremendous support provided both in the front and back of the body, the device is yet comfortable and can be worn easily during sporting activity such as golf or tennis for the benefit of the wearer. In summary, the device allows with a preformed lumbar support member and preformed abdominal support member that can be snugly affixed to the wearer. The perfect back configuration benefits the user by realigning back muscles and the back spinal column while toning muscles around the back and the spinal column.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A brace for supporting a user's abdomen and lower back comprising:
   abdominal support member for supporting the abdominal region of the user, said member having a first end and a second end, and including a plurality of adjustment slots adjacent to each of said first and second ends;
   lumbar support member, having a first end and a second end, and including a plurality of adjustment slots adjacent to each of said first and second ends;
   said lumbar support member incorporating a convex hemispherical dome sized for protrusion into the central lumbar region of the user for supporting and aligning the skeletal and muscular structure of the user's lower back;
   first and second belts attached to said adjustment slots at said first ends and said second ends respectively of said lumbar and said abdominal support members for increasing support pressure of said abdominal support member and said lumbar support member against the abdominal and lumbar regions of the user respectively.

2. The brace according to claim 1, wherein said abdominal and lumbar support members are made of thermal plastic which are preformed in anatomically conforming configurations in standard sizes each sized lumbar support member having a proportionally sized, protruding hemispherical dome, to precisely fit and support the user.

3. The brace according to claim 1 wherein said abdominal and lumbar support members are substantially rectangular and further include rounded tapered edges for preventing unwanted pressure during wear.

4. The brace according to claim 1, wherein said abdominal and lumbar support members include vents for allowing the circulation of air under each respective member.

* * * * *